United States Patent [19]

Bien

[11] Patent Number: 5,704,929
[45] Date of Patent: Jan. 6, 1998

[54] ABSORBENT ARTICLE HAVING SELECTIVELY ALTERABLE DIMENSIONS

[75] Inventor: Denise Jean Bien, Cincinnati, Ohio

[73] Assignee: The Procter & Gamble Company, Cincinnati, Ohio

[21] Appl. No.: 726,504

[22] Filed: Oct. 7, 1996

[51] Int. Cl.⁶ .................................................. A61F 13/15
[52] U.S. Cl. ............................. 604/385.1; 604/387
[58] Field of Search ........................ 604/383, 385.1, 604/386, 387, 389, 396, 395, 385.2, 304–307; 602/903

[56] References Cited

U.S. PATENT DOCUMENTS

| | | | |
|---|---|---|---|
| 3,049,228 | 8/1962 | Burnett | 604/389 |
| 3,143,208 | 8/1964 | Sizemore, Jr. | 602/903 |
| 3,211,142 | 10/1965 | Pherson et al. | 604/364 |
| 4,122,552 | 10/1978 | Tedserd | 604/389 |
| 4,596,570 | 6/1986 | Jackson et al. | |
| 4,597,759 | 7/1986 | Johnson | 604/389 |

FOREIGN PATENT DOCUMENTS 0464857  1/1992  European Pat. Off. ............ 604/392

Primary Examiner—John G. Weiss
Assistant Examiner—K. M. Reichle
Attorney, Agent, or Firm—Jeffrey V. Bamber; Steven W. Miller; Jacobus C. Rasser

[57] ABSTRACT

Absorbent articles such as pantiliners, panty liners, and incontinence pads are disclosed. More particularly, the present invention relates to absorbent articles, such as pantiliners, that can have portions thereof removed or otherwise manipulated to change, and particularly reduce, the dimensions of the absorbent article so that they can fit a variety of panty sizes and styles. In a preferred embodiment, the pantiliner is adjusted in size by tearing the absorbent article along one or more perforation lines and removing the portions of the absorbent article that lie outboard of the perforation lines.

5 Claims, 1 Drawing Sheet

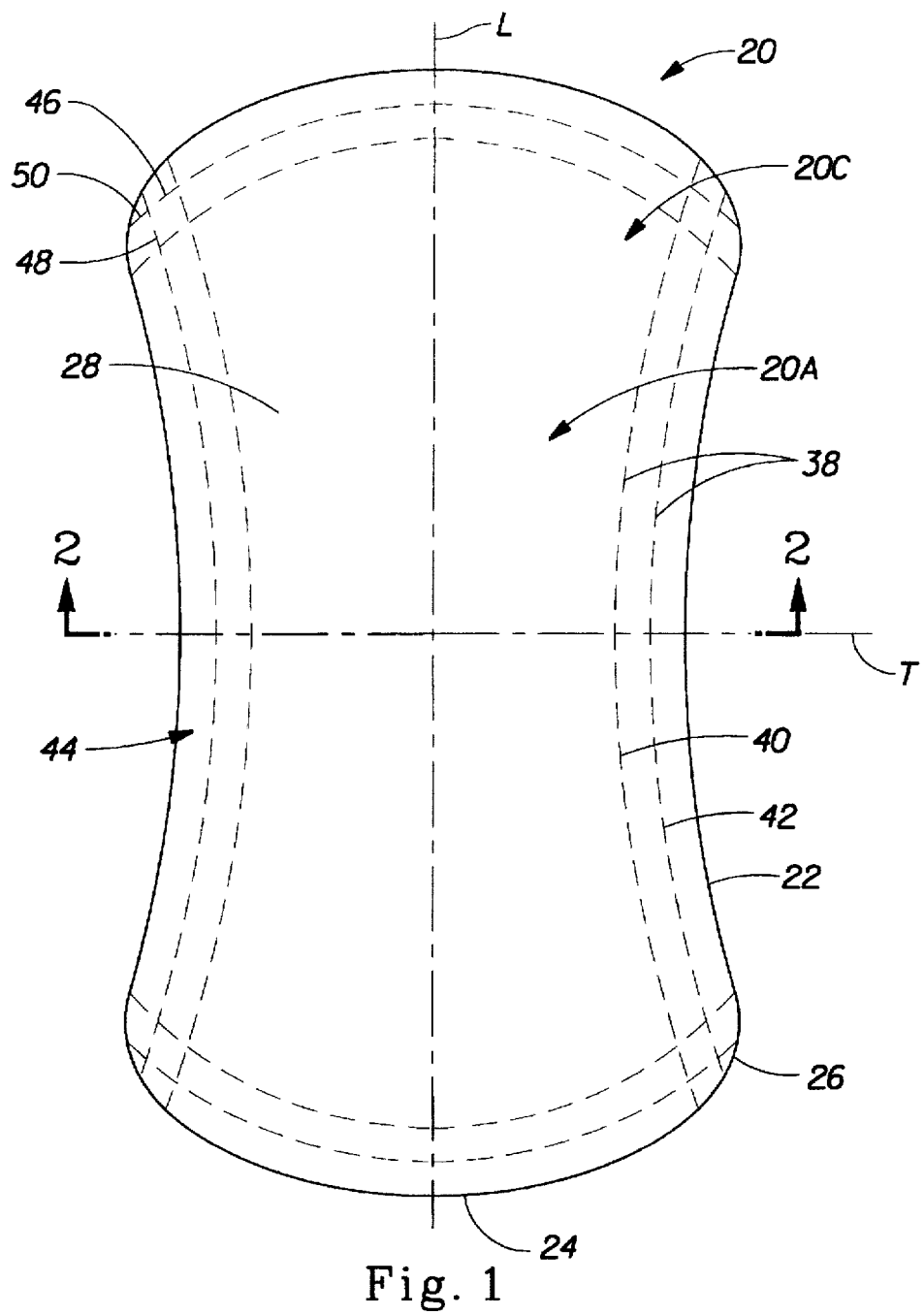
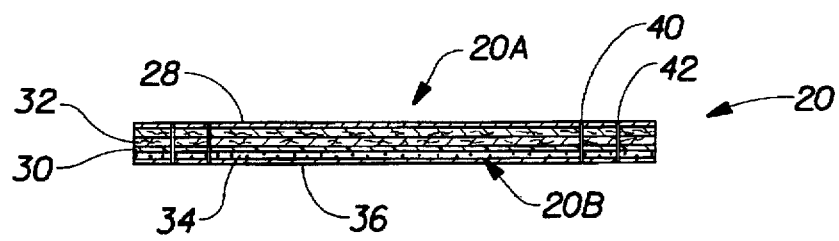

ABSORBENT ARTICLE HAVING SELECTIVELY ALTERABLE DIMENSIONS

FIELD OF THE INVENTION

The present invention relates to absorbent articles such as sanitary napkins, pantiliners, and incontinence pads. More particularly, the present invention relates to absorbent articles, particularly pantiliners, that can have portions thereof removed or otherwise manipulated to change, and preferably reduce, the dimensions of the absorbent article.

BACKGROUND OF THE INVENTION

Absorbent articles such as sanitary napkins and pantiliners are well known for their use in absorbing and retaining liquid discharges from the human body. Sanitary napkins are used principally during a woman's menstrual period to contain menses and other vaginal discharges so as to protect garments from soiling. However, many women experience frequent or daily, light vaginal discharges between their menstrual periods. While sanitary napkins are an efficient way to deal with the problem, products such as pantiliners (or "panty liners") have been developed specifically to protect a woman's garments from soiling due to these light discharges and to provide supplemental protection for garments when other catamenial products are used during the menstrual period.

Pantiliners are generally small in size, absorbent and comfortable to use. Generally, pantiliners are intended to be affixed to the crotch region of the user's undergarment and comprise an absorbent core, a topsheet, and an impermeable backsheet located on the pantiliner's garment-facing side that acts as a fluid barrier to absorbed body liquids to protect the user's garments from staining. Examples of pantiliners are described in U.S. Pat. No. 4,681,578 entitled "Pantiliner With Ventilation Areas" issued to Anderson, et al. on Jul. 21, 1987; U.S. Pat. No. 4,738,676 entitled "Pantiliner" issued to Osborn on Apr. 19, 1988; PCT Publication No. WO 96/10974 entitled "Flexible and Stretchable Absorbent Articles and Their Fixation To Undergarments", published in the name of Querqui on Apr. 18, 1996; PCT Publication No. WO 96/14034 entitled "Breathable Backsheet Design for Disposable Absorbent Articles", published in the name of Depner, et al. on May 17, 1996; PCT Publication No. WO 96/14036 entitled "Flexible and Breathable Absorbent Articles and Their Fixation to Undergarments", published in the name of Hirsch on May 17, 1996; PCT Publication No. WO 96/14036 entitled "Flexible and Water Vapour Permeable Absorbent Articles and Their Fixation to Undergarments", published in the name of Querqui on May 17, 1996; and in PCT Publication No. WO 96/14037 entitled "Breathable Dual Layer Backsheet Design for Disposable Absorbent Articles", published in the name of Depner, et al. on May 17, 1996.

Currently, pantiliners must fit a wide variety of individual panty sizes. In addition, there are a wide variety of panty styles. Thus, even if a woman has panties that are of only one size, it is likely that she will have more than one style of panty. Since the dimensions of the different styles of panties available, particularly the panty crotch dimensions thereof, can vary widely, pantiliners used by each wearer must often fit a variety of individual panty styles. Further, there are also significant differences in the styles of panties worn by women in different geographies.

Thus, a need exists for an absorbent article, particularly a pantiliner, that can be adjusted in size by a wearer to fit individual panty sizes and styles.

It is, therefore, an object of the present invention to provide an absorbent article, particularly a pantiliner, that can be adjusted in size by a wearer to fit individual panty sizes and styles.

This and other objects of the present invention will be more readily apparent when considered in reference to the following description and when taken in conjunction with the accompanying drawings.

SUMMARY OF THE INVENTION

The present invention relates to absorbent articles such as sanitary napkins, pantiliners, and incontinence pads. More particularly, the present invention relates to absorbent articles, particularly pantiliners, that can have portions thereof removed or otherwise manipulated to change, and particularly reduce, the dimensions of the absorbent article so that they can fit a variety of panty sizes and styles.

The absorbent article comprises a liquid pervious topsheet, a liquid impervious backsheet joined to the topsheet, and an absorbent core positioned between the topsheet and the backsheet. The absorbent article can be adjusted in size by a wearer to fit their individual panty size. In a preferred embodiment, the absorbent article is a pantiliner, and the means for adjusting the size of the absorbent article comprises at least one perforation line that is located so that a portion of said absorbent article is outboard of the perforation line. The absorbent article is adjusted in size by tearing the absorbent article along the perforation line and removing the portion of the absorbent article outboard of the perforation line.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

FIG. 1 is a top plan view of a pantiliner of the present invention.

FIG. 2 is a cross-sectional view of the sanitary napkin shown in FIG. 1 taken along line 2—2 of FIG. 1.

DETAILED DESCRIPTION OF THE INVENTION

FIGS. 1 and 2 show one preferred embodiment of a disposable absorbent article of the present invention, pantiliner 20. As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner).

The pantiliner 20 has two surfaces, a liquid pervious body-contacting surface or "body surface" 20A and a liquid impervious garment surface 20B. The pantiliner 20 is shown in FIG. 1 as viewed from its body surface 20A. The body surface 20A is intended to be worn adjacent to the body of the wearer. The garment surface 20B of the pantiliner 20 (shown in FIG. 2) is on the opposite side and is intended to be placed adjacent to the wearer's undergarments when the pantiliner 20 is worn. The pantiliner 20 has two spaced apart longitudinal edges 22, two spaced apart transverse or end edges (or "ends") 24, which together form the periphery 26 of the pantiliner 20.

The pantiliner 20 has two centerlines, a longitudinal centerline L and a transverse centerline T. The term "longitudinal", as used herein, refers to a line, axis or direction in the plane of the pantiliner 20 that is generally aligned with (e.g., approximately parallel to) a vertical plane which bisects a standing wearer into left and right body halves when the pantiliner 20 is worn. The terms "transverse" or "lateral" used herein, are interchangeable, and refer to a line, axis or direction which lies within the plane of the pantiliner 20 that is generally perpendicular to the longitudinal direction. It should be understood that the pantiliner 20 shown in the drawings is merely one preferred embodiment, and that the present invention is not limited to absorbent articles of the type or having the specific configuration shown in the drawings.

The pantiliner 20 comprises a base pantiliner 20C and several removable sections (described in greater detail below). The base pantiliner 20C comprises that portion of the pantiliner that remains after all the removable sections have been removed. The pantiliner 20 of the present invention, thus, comprises the base pantiliner 20C and the removable sections. FIG. 2 shows the individual components of the pantiliner 20 of the present invention. The pantiliner 20 generally comprises at least three primary components. These include a liquid pervious topsheet 28, a liquid impervious backsheet 30, and an absorbent core 32 positioned between the topsheet 28 and the backsheet 30.

The topsheet 28 is compliant, soft feeling, and non-irritating to the wearer's skin. Further, the topsheet 28 is liquid pervious permitting liquids (e.g., menses and/or urine) to readily penetrate through its thickness. A suitable topsheet 28 may be manufactured from a wide range of materials such as cellulosic fobrous structures (as described below); woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

Apertured formed films are often preferred for the topsheet because they are pervious to body exudates and, if properly apertured, have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; and U.S. Pat. No. 5,006,394 "Multilayer Polymeric Film" issued to Baird on Apr. 9, 1991. Preferred apertured film topsheets are described in one or more of the above patents and marketed on sanitary napkins by The Procter & Gamble Company of Cincinnati, Ohio as "DRI-WEAVE" topsheets.

In a preferred embodiment of the present invention, the body surface of the topsheet 28 is hydrophilic so as to help liquid to transfer through the topsheet 28 faster than if the body surface was not hydrophilic. This diminishes the likelihood that menstrual fluid will flow off the topsheet rather than flowing into and being absorbed by the absorbent core. The body surface of the topsheet 28 can be made hydrophilic by treating it with a surfactant in any of the manners described in U.S. Pat. No. 4,950,254 issued to Osborn.

The absorbent core 32 may be any absorbent means which is capable of absorbing or retaining liquids (e.g., menses and/or urine). The absorbent core 32 may be manufactured in a wide variety of sizes and shapes (e.g., rectangular, oval, hourglass, dog bone, asymmetric, etc.) and from a wide variety of liquid-absorbent materials commonly used in pantiliners, sanitary napkins, and other absorbent articles. One commonly used absorbent material in pantiliners, is comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core may also be varied (e.g., the absorbent core may have varying caliper zones), hydrophilic gradients, superabsorbent gradients, or lower density and lower average basis weight acquisition zones; or may comprise one or more layers or structures). The total absorbent capacity of the absorbent core should, however, be compatible with the design loading and the intended use of the absorbent article. Further, the size and absorbent capacity of the absorbent core may be varied to accommodate different uses such as incontinence pads, pantiliners, regular sanitary napkins, or overnight sanitary napkins.

The backsheet 30 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 30 prevents the exudates absorbed and contained in the absorbent core 32 from wetting articles which contact the pantiliner 20 such as pants, pajamas and undergarments. The backsheet 30 may thus comprise a woven or nonwoven material, polymeric films such as thermoplastic films of polyethylene or polypropylene, or composite materials such as a film-coated nonwoven material. Preferably, the backsheet 30 is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation DH 226. The backsheet may also be embossed and/or matte finished to provide a more clothlike appearance. Further, the backsheet 30 may permit vapors to escape from the absorbent core 32 (i.e., it may be breathable) while still preventing exudates from passing through the backsheet 30.

In the preferred embodiment shown in the drawings, the topsheet 28 comprises a cellulosic fibrous structure. A preferred cellulosic fibrous structure is provided with two (or more) regions, one of which is a network region which is essentially continuous, macroscopically monoplanar, and is formed into a preselected pattern. The other region comprises discrete low density zones or apertures. A suitable cellulosic fibrous structure is one that is made according to the description of U.S. Pat. No. 4,514,345, issued to Johnson, et al. in Columns 8–9 using the foraminous member shown in FIG. 4 of the Johnson, et al. patent. Other suitable cellulosic structures can be made according to the description in U.S. Pat. No. 5,425,025 issued to Trokhan, et al. In this preferred embodiment, the absorbent core 32 comprises two layers of 35 pound basis weight Ft. Howard tissue obtained from Fort Howard Corporation of Green Bay, Wis. Other suitable tissues can be obtained from Merfin Hygiene Products Ltd., Delta, BC, Canada. The backsheet 30 preferably comprises a sheet of Clopay DH 226 polyethylene film. The topsheet 28, the backsheet 30, and the absorbent core 32 may be assembled in a variety of configurations known in the art (including so called "sandwich" products and "tube" products).

The topsheet 28 and the backsheet 30 are positioned adjacent the body surface and the garment surface, respectively, of the absorbent core 32 and are preferably joined thereto and to each other by attachment means such as those well known in the art. For example, the topsheet 28 and/or the backsheet 30 may be secured to the absorbent core 32 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986 entitled "Disposable Waste-Containment Garment", which issued to Minetola, et al. on Mar. 4, 1986. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment means may comprise heat bonds, pressure bonds, ultrasonic bonds, dynamic mechanical bonds, or any other suitable attachment means or combinations of these attachment means as are known in the art.

The garment surface 20B of the pantiliner 20 may include, and preferably does include, a fastener for attaching the pantiliner to the wearer's undergarment. FIG. 2 shows the panty fastener 34 that is adapted to secure the pantiliner 20 to the crotch region of an undergarment. Any types of fasteners known in the art can be used. Fasteners comprising adhesives have been found to work well for this purpose, with pressure-sensitive adhesives being preferred. The panty fastener 34 can be provided in any suitable configuration. In the preferred embodiment shown in FIGS. 1 and 2, the panty fastener 34 covers substantially all of the backsheet 30. Before the pantiliner 20 is placed in use, if an adhesive fastener is used, the adhesive is typically covered with a removable cover strip or release liner 36 in order to keep the adhesive from sticking to a surface other than the crotch portion of the panty prior to use. Suitable release liners are described in the U.S. Pat. No. 4,917,697.

The pantiliner 20 can be of any suitable size and shape. Preferably, in the embodiment shown in the drawings, the base pantiliner 20C is about 163 mm long as measured in the longitudinal direction, and about 51 mm wide (measured in the transverse direction) at its narrowest point. The overall pantiliner 20 is about 185 mm long as measured in the longitudinal direction, and about 73 mm wide at its narrowest point.

The pantiliner 20 has portions or sections thereof that can be removed, or otherwise manipulated by the user to change, and particularly to reduce, the dimensions of the pantiliner 20. In the embodiment shown in the drawings, the pantiliner 20 is provided with a plurality of perforations arranged in the form of perforation lines, designated generally by reference number 38. Preferably, the perforation lines 38 in this embodiment comprise two perforation lines, comprising a first (or "inner") perforation line 40 and a second (or "outer") perforation line 42. The first and second perforation lines 40 and 42 may be provided in any suitable configuration. Preferably, the perforation lines are provided in the same general configuration as the periphery 26 of the pantiliner. In the preferred embodiment shown in FIG. 1, the inner perforation line 40 is spaced a distance of about 10 mm inward (or "inboard") from the periphery 26 of the pantiliner. The outer perforation line 42 is spaced a distance of about 5 mm inward from the periphery 26 of the pantiliner 20. The pantiliner 20 can, thus, be adjusted in size about 20 mm in its longitudinal dimension and in its transverse dimension. In other embodiments, the size of the pantiliner (or other absorbent article) can be adjusted in any other suitable mounts.

The perforation lines 38 are preferably comprised of a plurality of spaced apart slits. The slits should be long enough to allow easy tearing and removal of the portions of the pantiliner located outboard of the perforation lines (designated generally by reference number 44) without leaving ragged edges along the sides of the pantiliner softer removal of the outer portions. The perforation lines 38 preferably extend completely through the pantiliner 20 and any release paper 36 covering the panty fastener 34 on the garment-facing side thereof 20B. In other embodiments, however, the perforation lines need not be formed into the release paper 36 so that the consumer only has a single piece of release paper to handle and dispose.

The perforation lines 38 are preferably provided with extensions (designated generally by reference number 46) that extend between the peripheral-shaped portions of the perforation lines and the periphery 26 of the pantiliner. These extensions 46 of the perforation lines 38 comprise longitudinally-oriented extensions 48 and laterally-oriented extensions 50. The longitudinally-oriented extensions 48, together with the perforation lines that they are extensions of, allow portions that make up the width of the pantiliner to be removed without altering the lengthwise dimension of the pantiliner. The laterally-oriented extensions 50 of the perforation lines, together with the perforation lines that they are extensions of, allow portions of the length of the pantiliner to be removed without altering the widthwise dimension of the pantiliner.

The pantiliner 20 of the present invention is used by comparing the size of the pantiliner to the size of the crotch of the wearer's panties. The wearer then removes any desired portions of the pantiliner located outboard of the perforation lines 38 so that the pantiliner will be of the size desired to fit into the wearer's panties. The release liner 36 on the remainder of the pantiliner is removed, and the pantiliner 20 is placed in a panty so that the adhesive (or other fastener) 34 contacts the panty and maintains the pantiliner in position within the panty during use.

Numerous alternative embodiments of the present invention are possible. For example, the absorbent article can have portions that are folded back at perforation lines, or other lines of weakness, rather than being removed at perforation lines. The panty fastener on the back of such folded back portions could secure the folded back portions to the remaining portion of the absorbent article.

In these or other alternative embodiments, the pantiliner, or other absorbent article, can be provided with odor control properties (for example, the pantiliner may comprise a mixture of zeolite A, absorbent gelling material, and polyethylene powder that is homogeneously blended and applied to the absorbent core). The pantiliner may also be flushable and incorporate the technology described in U.S. patent application Ser. No. 08/561,989 entitled "Water Dispersible and Flushable Absorbent Article", filed in the name of Christon, et al. on Nov. 22, 1995. The pantiliner may also be comprised of one or more extensible components such as those sanitary napkins, and the like described in U.S. patent application Ser. No. 07/915,133 filed Jul. 23, 1992, in the name of Osborn, et al. (PCT Publication No. WO 93/01785, published Feb. 4, 1993), now pending in the form of allowed continuation application Ser. No. 08/503,895, filed on Jul. 18, 1995; and U.S. patent application Ser. No. 07/915,284 filed Jul. 23, 1992, in the name of Osborn, et al. (PCT Publication No. 93/01786, published Feb. 4, 1993), now pending in the form of allowed divisional application Ser. Nos. 08/472,156 and 08/476,238, filed on Jun. 7, 1995.

In these or other alternative embodiments of the present invention, the pantiliner can have two flaps each of which are adjacent to and extend laterally from the side edge of the absorbent core. The flaps are preferably configured to drape over the edges of the wearer's panties in the crotch region so that the flaps are disposed between the edges of the wearer's panties and the thighs. The flaps serve at least two purposes. First, the flaps help serve to prevent soiling of the wearer's body and panties by menstrual fluid, preferably by forming a double wall barrier along the edges of the panty. Second, the flaps are preferably provided with attachment means on their garment surface so that the flaps can be folded back under the panty and attached to the garment facing side of the panty or to the other flap. In this way, the flaps serve to keep the absorbent article properly positioned in the panty. The flaps can be constructed of various materials including materials similar to the topsheet, backsheet, tissue, or combination of these materials. Further, the flaps may be a separate element attached to the main body of the absorbent article or can comprise extensions of the topsheet and backsheet (i.e., unitary). A number of absorbent articles having flaps suitable or adaptable for use with the absorbent article of the present invention are disclosed in U.S. Pat. No. 4,687,478 entitled "Shaped Sanitary Napkin With Flaps", which issued to Van Tilburg on Aug. 18, 1987; U.S. Pat. No. 4,589,876 entitled "Sanitary Napkin", which issued to Van Tilburg on May 20, 1986; and U.S. Pat. No. 4,608,047, entitled "Sanitary Napkin Attachment Means", which issued to Mattingly on Aug. 26, 1986. The absorbent articles can be provided with a feature, such as perforations, that allows the side of the flaps to be adjusted.

Other embodiments of the absorbent articles described herein are also possible. For example, in alternative embodiments, instead of being provided with flaps, the absorbent article could be provided with undergarment covering components or ("side wrapping elements") that have a smaller span than conventionally sized flaps and that do not have to be manipulated by the wearer when placed in the wearer's undergarments. These side wrapping elements can also be provided with a feature that allows them to be adjusted in size. Absorbent articles having side wrapping elements are described in allowed U.S. patent application Ser. No. 08/096,121 entitled "Absorbent Articles Having Panty Covering Components That Naturally Wrap the Sides of Panties" filed Jul. 22, 1993, in the name of Lavash, et al. (PCT Publication No. WO 94/02096, published Feb. 3, 1994); U.S. patent application Ser. No. 08/124,180 entitled "Absorbent Articles Having Panty Covering Components Comprising Extensible Web Materials Which Exhibit Elastic-Like Behavior" filed Sep. 17, 1993, in the name of Mansfield, et al. (PCT Publication No. WO 95/07675, published Mar. 23, 1995); and U.S. Pat. No. 5,558,663 entitled "Absorbent Articles Having Undergarment Covering Components With Zones of Extensibility" issued to Weinberger, et al. on Sep. 24, 1996.

As discussed above, the adjustable feature of the present invention can be provided on other types of absorbent articles, such as sanitary napkins and incontinence articles. The term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). As used herein, the term "pudendal" refers to the externally visible female genitalia. Preferred sanitary napkin configurations are described generally in U.S. Pat. No. 4,950,264, "Thin, Flexible Sanitary Napkin" issued to Osborn on Aug. 21, 1990; U.S. Pat. No. 4,425,130, "Compound Sanitary Napkin" issued to DesMarais on Jan. 10, 1984; U.S. Pat. No. 4,321,924, and "Bordered Disposable Absorbent Article" issued to Ahr on Mar. 30, 1982. Interlabial devices which reside within, or partially within and partially external of the wearer's vestibule are also within the scope of this invention.

The term "incontinence article" refers to pads, undergarments (pads held in place by a suspension system of same type, such as a belt, or the like), inserts for absorbent articles, capacity boosters for absorbent articles, briefs, bed pads, and the like, regardless of whether they are worn by adults or other incontinent persons. Suitable incontinence articles that can be provided with the adjustable feature described herein are disclosed in U.S. Pat. No. 5,300,054 issued to Feist, et al. on Apr. 5, 1994 and U.S. Pat. No. 5,304,161 issued to Noel, et al. Apr. 19, 1994.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

While particular embodiments of the present invention have been illustrated and described, it would be obvious to those skilled in the art that various other changes and modifications can be made without departing from the spirit and scope of the invention.

What is claimed is:

1. An absorbent article for wearing in a crotch region of a wearer's undergarment, said absorbent article comprising a periphery having a configuration, a longitudinal centerline, a longitudinal dimension extending in a longitudinal direction, longitudinal side edges, a transverse dimension extending in a transverse direction, end edges, a liquid pervious topsheet, a liquid impervious backsheet joined to said topsheet, an absorbent core positioned between said topsheet and said backsheet, and at least one perforation line located inboard of said periphery and extending along said entire periphery, said at least one perforation line extending perpendicular to the longitudinal and transverse directions completely through said absorbent article along said end edges and said longitudinal side edges allowing said absorbent article to be reduced in size by a wearer to fit individual undergarment sizes.

2. The absorbent article of claim 1 wherein said absorbent article is adjusted in size by tearing said absorbent article along said at least one perforation line and removing said portion of said absorbent article located outboard of said at least one perforation line.

3. The absorbent article of claim 2 wherein said at least one perforation line has the same configuration as said periphery of said absorbent article.

4. The absorbent article of claim 3 wherein said absorbent article comprises more than one perforation line having the same configuration as said periphery of said absorbent article.

5. The absorbent article of claim 1 wherein said absorbent article is a pantiliner.

* * * * *